United States Patent [19]

Gaffar

[11] 4,272,512

[45] Jun. 9, 1981

[54] ANTIGINGIVITIS COMPOSITION

[75] Inventor: Abdul Gaffar, Somerset, N.J.

[73] Assignee: Colgate-Palmolive Company, New York, N.Y.

[21] Appl. No.: 117,409

[22] Filed: Jan. 31, 1980

[51] Int. Cl.³ .................. A61K 7/16; A61K 31/19; A61K 31/505

[52] U.S. Cl. .................. 424/49; 424/251; 424/305

[58] Field of Search ................ 424/49–58, 424/251, 305

[56] References Cited

FOREIGN PATENT DOCUMENTS

| | | |
|---|---|---|
| 2208055 | 9/1972 | Fed. Rep. of Germany . |
| 2242553 | 3/1974 | Fed. Rep. of Germany . |
| 47-01479 | 1/1972 | Japan . |
| 49-39818 | 10/1974 | Japan . |
| 1321399 | 6/1973 | United Kingdom . |

OTHER PUBLICATIONS

Slovokhotnova, Chem. Abstr. 71 #10826d, (1969), Role of B-Vitamins in Preventing Dental Caries.

Vogel et al., Chem. Abstr. 86 #65745s, (1977), The Effect of Folic Acid on Gingival Health.

Dreizen et al., J. Dent. Res. 49(3), 616–620, May, Jun. 1970, The Effect of Folic Acid Deficiency on the Marmoset Oral Mucosa, Abstr. In. Chem. Abstr. 73 #106848e, (1970).

Koehlor, Chem. Abstr. 80 #149035z, (1974), of Ger. Offen. 2,342,553, Mar. 7, 1974.

Iwasaki et al., C.A. 83 #33030b, (1975), of Japan 74/39818, Oct. 29, 1974.

Okano et al., C.A. 78 #47669a, (1973), of Japan 72/01479, Jan. 14, 1972.

*Primary Examiner*—Shep K. Rose
*Attorney, Agent, or Firm*—Herbert S. Sylvester; Murray M. Grill; Robert L. Stone

[57] ABSTRACT

An oral composition adapted to inhibit symptoms of gingivitis, especially gingival bleeding, comprising an oral vehicle and effective amounts of tranexamic acid and folic acid.

9 Claims, No Drawings

ANTIGINGIVITIS COMPOSITION

This invention relates to a non-antibacterial oral composition which promotes oral hygiene, and especially to such a composition for treating and controlling certain periodontal diseases, for example inflammation, bleeding and/or swelling of the gums as in gingivitis and parulis, gingival retraction, ulatrophy, etc. Types of gingivitis include afunctional gingivitis, gingivitis marginal and cotton-roll gingivitis.

Periodontitis, or pyorrhea, is a disease affecting the supporting tissues of the teeth including the gingiva, the membrane lining the sockets which the teeth lie, and the bones surrounding the teeth. The disease may initially be associated with conditions of constant irritation of the gingiva by dental plaque, food impaction, poor dental restorations, traumatic occlusion, or chemical irritants.

The gums may be seriously harmed by deposits of dental plaque, a combination of minerals and bacteria found in the mouth. The bacteria associated with plaque can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accummulate. It is also possible for food to accumulate in these pockets, thereby providing nourishment for increased growth of bacteria and production of endotoxins and destructive enzymes. The pus that forms in this process is capable of destroying gum and bone tissue. A variety of bacteria are generally found to be present during the active stages of periodontal disease. Such organisms as streptococci, staphylococci and gram negatives are usually present, and are found in the purulent discharge as well as in the involved tissue, and may be absorbed into the general system through the lymphatics or venous blood stream.

The progression of the pyorrheic process usually begins with gingivitis, initiating at the margins of the gums, in which the gingiva become more tender and sensitive, and appear flabby, inflamed and swollen. Periodontal pockets become apparent, and infection takes place in these pockets. Effective control and prevention of gingivitis accordingly constitutes a desideratum for the prevention of further periodontal diseases.

A multitute of materials have been previously proposed and employed for controlling oral diseases and malfunctions such as plaque, calculus, tartar, caries, halitosis, and periodontal diseases such as gingivitis and pyorrhea, but none have been entirely satisfactory. For example some of such materials have been found to be unstable in the presence of the anionic surface active agents generally present in conventional oral preparations. A number of such materials such as the cationic quaternary ammonium agents exert an antibacterial function which undesirably tends to disrupt or destroy the normal microflora of the mouth and/or the digestive system.

Trans-4-(aminomethyl)cyclohexane-1-carboxylic acid, hereinafter referred to as tranexamic acid or TA, of the structural formula

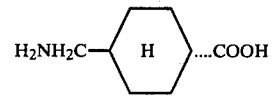

has been shown to be a highly effective agent for controlling, inhibiting or preventing gingivits and other periodontal diseases, halitosis, and the like; see e.g. Jap. Pat. Appln. Publn. No. 39818/74. This compound is non-antibacterial and unlike antibacterials, it is a specific inhibitor of gingival inflammation, bleeding and/or swelling.

TA is a white crystalline powder having a decomposition temperature of about 380°–390° C. It has characteristic infra red absorption bands at 1637, 1535 and 1383 cm$^{-1}$. It is highly soluble in water, sparingly soluble in heated ethanol, and substantially insoluble in most of the organic solvents. A method or its synthesis or its isolation from cis-trans mixtures thereof is disclosed in U.S. Pat. No. 3,499,925.

The atigingivitis effects, and especially the reduction or inhibition of gingival bleeding, of TA are however not as high or complete as could be desired, and it is accordingly an object of this invention to provide a TA containing oral composition, and method of use thereof, which is even more effective against the symptons of gingivitis, especially gingival bleeding. Other objects and advantages will appear as the description proceeds.

The attainment of the above objects is made possible by this invention which is based upon my discovery that the inclusion of folic acid as an additive in a TA-containing oral composition unexpectedly improves the anti-gingivitis effects, and especially inhibition of gingival bleeding, of the TA.

In accordance with certain of its aspects, this invention relates to an oral composition adapted to inhibit symptoms of gingivitis, especially gingival bleeding, comprising an oral vehicle and effective amounts of TA and folic acid, Folic acid is a known anti-irritant and anti-inflammatory material. It is a conjugate bound to up to seven molecules of glutamic acid and has the structural basic formula:

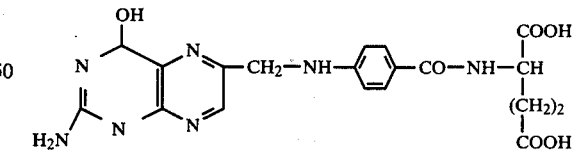

It was reported by R. Vogel et al of New Jersey Dental School, Newark New Jersey, In AADR Abstracts 1977, 34 "Effect of Folic Acid Rinse On Gingival Health", and IADR Abstracts 1977, 565 "Folic Acid and Experimental Produced Gingivitis", that folic acid can be directly absorbed by the gingiva from a rinse solution resulting in a reduction in gingival inflammation.

Folic acid has however been found to be not as effective as TA against gingivitis, especially gingival bleeding, and it is accordingly highly surprising that the compositions of this invention containing TA and folic acid as additive are more effective against such symptoms than compositions containing either TA or folic acid alone. The TA- folic acid combination may accordingly be considered synergistic.

The concentration of the folic acid additive in oral compositions can range widely, typically upward from about 0.001% by weight with no upper limit except as dictated by cost or incompatibility with the vehicle. Effective and/or optimal stain-inhibiting amounts of this additive in any particular instance is readily determinable by routine experimentation. Typically, concentrations of about 0.001% to about 10%, preferably about 0.01% to 5%, more preferably about 0.02% to about 1.0%, by weight are utilized. Oral compositions which in the ordinary course of usage could be accidentally ingested preferably contain lower concentrations of these additives. Thus, a mouthwash in accordance with this invention preferably contains less than about 2 weight % of the additive, preferably about 0.05 to about 1.5 weight %. Dentifrice compositions, topical solutions and prophylactic pastes, the latter to be administered professionally, can preferably contain 0.5 to about 5 weight % of the additive. The folic acid additive may be employed in free acid form or in the form of an orally acceptable salt thereof, preferably water soluble, e.g. of the type discussed below with respect to the TA agent.

The TA agent may be employed in free acid form or in the form of an orally acceptable salt thereof, preferably water soluble, such as with an alkali metal (e.g. Na or K), ammonium, or $C_1$-$C_{18}$ mono-, di-or tri-substituted ammonium (e.g. alkanol substituted such as mono-, di- or tri-ethanolammonium) cation. Typically, about 0.001 to about 10.0%, preferably about 0.01 to about 5.0%, and more preferably about 1.0 to about 3.0%, by weight of this TA agent are employed in the oral compositions of this invention.

In certain highly preferred forms of the invention, the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water-alcohol mixture in this type of preparation is typically in the range of from about 70 to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying dental enamel.

Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate, tricalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns, a mean particle size of up to 1.1 microns, and a surface area of up to 50,000 $cm^2$/gm., silica gel, complex amorphorus alkali metal aluminosilicate, hydrated alumina, dicalcium phosphate.

Alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner, as illustrated by Thorpe's Dictionary of Applied Chemistry, Volume 9, fourth Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 10 to about 99% by weight of the oral preparation. Preferably, it is present in amounts ranging from about 10 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antigingivitis agent and additive should be compatible with the other components of the preparation. Thus, in a toothpaste, the liquid vehicle may comprise water and humectant typically in an amount ranging from about 10 to about 90% by weight of the preparation. Glycerine, sorbitol, or polyethylene glycol may also be present as humectants or binders. Particularly advantageous liquid ingredients are polyethylene glycol and polypropylene glycol. Also advantageous are liquid mixtures of water, glycerine and sorbitol.

In clear gels where the refractive index is an important consideration, about 3–30% by weight of water, 0 to about 80% by weight of glycerine, and about 20–80% by weight of sorbitol is preferably employed. A gelling agent, such as natural or synthetic gums or gum-like materials, typically Irish moss, sodium carboxymethylcellulose, methyl cellulose, hydroxyethyl cellulose, gum tragacanth, polyvinylpyrrolidone, starch, and preferably hydroxypropyl methyl cellulose and the Carbopols (e.g. 934,940 and 941), etcetera is usually present in toothpaste in an amount up to about 1% by weight, preferably in the range of from about 0.5 to about 5%. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0 may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

The oral compositions of this invention may contain a non-soap synthetic sufficiently water soluble organic anionic or nonionic surfactant in concentrations generally ranging from about 0.05 to about 10, preferably about 0.5 to about 5, weight percent, to promote wetting, detersive and foaming properties. U.S. Pat. No. 4,041,149 discloses such suitable anionic surfactants in col. 4, lines 31–38, and such suitable nonionic surfactants in col. 8, lines 30–68 and col. 9, lines 1–12, which passages are incorporated herein by reference thereto.

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, calcium fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type or oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013 to 0.1% and most preferably about 0.0013 by weight, of fluoride.

It should at this point be noted that the inclusion of a fluorine-providing compound especially MFP (sodium monofluorophosphate), in the oral compositions of this invention must be highly judicious and selective since it has been found that such inclusion often results in oral compositions which turn yellow or brown upon aging and/or storage, apparently due to the effect of the F-containing compound on the stability of the TA agent.

Various other materials may be incorporated in the oral preparations of this invention, subject to the above. Examples are whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed, also subject to the above. Examples of suitable flavoring constituents are flavoring oils, e.g., oils of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, sodium cyclamate, perillartine, APM (aspartylphenylalanine, methyl ester) and saccharin. Suitably, flavor and sweetening agents may together comprise from about 0.1 to 5% or more of the preparation.

In preparing the oral compositions of this invention comprising the above-defined combination or antigingivits agents and additive in an oral vehicle which typically includes water, it is preferred to add the additive after the other ingredients (except perhaps some of the water) are mixed or contacted with each other.

For instance, a mouthrinse or mouthwash may be prepared by mixing ethanol and water with flavoring oils, nonionic surfactant, humectant, TA antigingivitis agent, sweetener, color and then the above-defined additive, followed by additional water as desired.

A toothpaste may be prepared by forming a gel with humectant, gum or thickener such as hydroxyethyl cellulose, sweetener and adding thereto polishing agent, flavor, antigingivitis agent, additional water, and then the above-defined additive.

In the practice of this invention an oral composition according to this invention such as a mouthwash or toothpaste containing TA antigingivitis agent in an amount effective to promote oral hygiene and the defined additive in the indicated antigingivitis and antigingival bleeding-improving amount, is applied regularly to dental enamel, preferably from about 1 to about 3 times daily at a pH of about 4.5 to about 9, generally about 5.5 to about 8, preferably about 6 to 8.

The following specific examples are further illustrative of the nature of the present invention, but it is understood that the invention is not limited thereto. All amounts and proportions referred to herein and the appended claims are by weight unless otherwise indicated.

EXAMPLE 1

40 pure bred beagle dogs 15 to 24 months old were anesthetized (Na-Nembutal) and given complete prophylaxis, that is, removal by scaling of hard and calcified deposits on the surfaces of teeth followed by polishing with pumice. A disclosing solution (Erythrosine-Provident Hoyt lab) was used to insure the complete removal of soft and hard deposits. The animals were kept on soft diet—a ground Purina dog chow soaked in water to form soft mush. No hard substances were permitted during the study. The animals were divided into 4 groups, each group treated twice daily with the test formulation. The dentrifrice formulations being tested and the placebo, were applied by gently brushing all surfaces of dentition. The mouth of each dog was kept closed for 1 minute to allow the contact of the solution with dentition. Approximately 5-6 ml. of formulation was applied per treatment. The treatment continued 5 days/week for the 24 week duration of the experiment. The study was double blind. Gingival bleeding was evaluated by applying gentle finger pressure on the gingivae. The results of this test are shown in TABLE I below.

TABLE 1

ORAL FORMULATIONS
(Parts by Weight)

| Example | Placebo (1) | (2) | (3) | (4) |
|---|---|---|---|---|
| Glycerin | 22.0 | 22.0 | 22.0 | 22.0 |
| Carboxymethyl cellulose | 1.1 | 1.1 | 1.1 | 1.1 |
| Na-benzoate | 0.5 | 0.5 | 0.5 | 0.5 |
| Na-saccharin | 0.2 | 0.2 | 0.2 | 0.2 |
| Dicalcium phosphate dihydrate | 50.0 | 50.0 | 50.0 | 50.0 |
| Na-lauryl sulfate | 1.5 | 1.5 | 1.5 | 1.5 |
| Flavor | 1.0 | 1.0 | 1.0 | 1.0 |
| Deionized water | 23.7 | 21.7 | 23.65 | 21.65 |
| Tranexamic acid |  | 2.0 |  | 2.0 |
| Folic acid |  |  | 0.05 | 0.05 |
| Bleeding units/ total units at risk | 14/198 | 7/200 | 10/197 | 4/160 |
| Total % | 7% | 3.5% | 5% | 2.5% |

The above results show the surprising synergism of the instant combination of tranexamic acid and folic acid for controlling gingivitis as evaluated by bleeding units.

EXAMPLE 5

|  | Wt. Percent |
|---|---|
| Hydroxypropyl methyl cellulose | 2 |
| Alumina (hydrated) | 49.0 |
| Polyethylene glycol 600 | 33.3 |
| Sodium benzoate | 0.5 |
| Sodium saccharin | 0.2 |
| Sodium lauryl sulfate | 1.5 |
| Folic acid | 0.05 |
| Tranexamic acid | 1.0 |
| Flavor* | 1.0 |
| Water to make 100% | |

*About 60% methyl salicylate, 32% menthol, 3% eugenol and 5% cineol.

EXAMPLE 6

|  | Wt. Percent |
|---|---|
| Insoluble metaphosphate | 48.0 |
| Polyethylene glycol 600 | 35.8 |
| Sodium benzoate | 0.5 |
| Sodium saccharin | 0.2 |
| Sodium laurylsulfate | 1.5 |
| Flavor* | 1.0 |
| Colloidal silica | 6.0 |
| Folic acid | 0.1 |
| Tranexamic acid | 1.0 |
| Water to make | 100% |

*About 60% methyl salicylate, 32% menthol, 3% eugenol and 5% cineol.

Examples 5 and 6 illustrate dentifrice formulations with lower gingivitis according to the invention. Other conventional components may be substituted or added as disclosed hereinbefore; e.g. polyethylene glycol 600 may be replaced by other gelling agents such as Pluronic F-127 (polyoxyethylenated polyoxypropylene), Laponite (Mg-Al-Si clay), or Carbopol 940.

This invention has been disclosed with respect to preferred embodiments, and it will be understood that modifications thereof obvious to those skilled in the art are to be included within the spirit and purview of this application and the scope of the appended claims.

I claim:

1. An oral composition adapted to inhibit symptoms of gingivitis comprising an oral vehicle and effective amounts of tranexamic acid and folic acid.

2. The oral composition of claim 1 containing about 0.001 to about 10.0 wt. % of tranexamic acid and about 0.001 to about 10.0 wt. % of folic acid.

3. The oral composition of claim 1 containing about 0.01 to about 5.0 wt. % of tranexamic acid and about 0.01 to about 5.0 wt. % of folic acid.

4. The oral composition of claim 1 containing about 1.0 to about 3.0 wt. % of tranexamic acid and about 0.02 to about 1.0 wt. % of folic acid.

5. The oral composition of claim 1 which is a mouthwash having a pH of about 4.5 to about 9 and an aqueous-alcohol vehicle.

6. The mouthwash composition of claim 5 containing about 0.001 to about 10.0 wt. % of tranexamic acid and about 0.001 to about 10.0 wt. % of folic acid.

7. The oral composition of claim 1 which is a toothpaste having a pH of about 4.5 to about 9 and containing a liquid vehicle, a gelling agent and a dentally acceptable polishing material.

8. The toothpaste composition of claim 7 containing about 0.001 to about 10.0 wt. % of tranexamic acid and about 0.001 to about 10.0 wt. % of folic acid.

9. A method of improving oral hygiene comprising applying to the oral cavity an effective amount of an oral composition as defined in claim 1.

* * * * *